United States Patent
Accetta et al.

(10) Patent No.: US 11,578,068 B2
(45) Date of Patent: Feb. 14, 2023

(54) OXADIAZOLE DERIVATIVES AS RHO-KINASE INHIBITORS

(71) Applicant: Chiesi Farmaceutici S.p.A., Parma (IT)

(72) Inventors: Alessandro Accetta, Parma (IT); Fabio Rancati, Parma (IT); Christine Edwards, Parma (IT); Elizabeth Anne Skidmore, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 204 days.

(21) Appl. No.: 16/954,968

(22) PCT Filed: Dec. 12, 2018

(86) PCT No.: PCT/EP2018/084548
§ 371 (c)(1),
(2) Date: Jun. 17, 2020

(87) PCT Pub. No.: WO2019/121233
PCT Pub. Date: Jun. 27, 2019

(65) Prior Publication Data
US 2020/0331912 A1    Oct. 22, 2020

(30) Foreign Application Priority Data
Dec. 18, 2017    (EP) .................................... 17208187

(51) Int. Cl.
| C07D 471/04 | (2006.01) |
| A61K 9/00 | (2006.01) |
| A61K 31/4375 | (2006.01) |
| A61K 31/444 | (2006.01) |
| A61K 45/06 | (2006.01) |

(52) U.S. Cl.
CPC ............ C07D 471/04 (2013.01); A61K 9/007 (2013.01); A61K 31/4375 (2013.01); A61K 31/444 (2013.01); A61K 45/06 (2013.01)

(58) Field of Classification Search
None
See application file for complete search history.

(56) References Cited

U.S. PATENT DOCUMENTS

| 2006/0241127 A1 | 10/2006 | Feurer et al. |
| 2008/0139595 A1 | 6/2008 | Schirok et al. |
| 2011/0207704 A1* | 8/2011 | Cusack ................ C07D 271/07 514/249 |

FOREIGN PATENT DOCUMENTS

| WO | WO 2004/039796 A1 | 5/2004 |
| WO | WO 2005/097790 A1 | 10/2005 |
| WO | WO 2006/009889 A1 | 1/2006 |
| WO | WO 2009/079008 A1 | 6/2009 |
| WO | WO 2010/032875 A2 | 3/2010 |
| WO | WO 2012/007539 A1 | 1/2012 |
| WO | WO 2014/118133 A1 | 8/2014 |
| WO | WO 2018/115383 A1 | 6/2018 |
| WO | WO 2018/138293 A1 | 8/2018 |

OTHER PUBLICATIONS

"Prevent." Macmillandictionary.com. Macmillan, 2021. Web. Dec. 16, 2021. (Year: 2021).*
Cleveland Clinic. "Asthma: Types, Causes, Symptoms, Diagnosis & Treatment." Retrieved Mar. 17, 2022. Retrieved from internet <URL: https://my.clevelandclinic.org/health/diseases/6424-asthma?view=print>; pp. 1-9. (Year: 2022).*
Medicinenet. "Pulmonary Fibrosis: Symptoms, Stages, Causes & Life Expectancy." Retrieved Mar. 17, 2022. Retrieved from internet <URL: https://www.medicinenet.com/pulmonary_fibrosis/article.htm>; 1-12. (Year: 2022).*
MedlinePlus. "COPD." Retrieved Mar. 17, 2022. Retrieved from internet <URL: https://medlineplus.gov/copd.html#>; pp. 1-12. (Year: 2022).*
Medscape. "Pulmonary Arterial Hypertension Treatment & Management." Retrieved on Mar. 17, 2022. Retrieved from internet <URL: https://emedicine.medscape.com/article/303098-treatment#d8>; pp. 1-6. (Year: 2022).*
Duong-Quy, S., et al., "Role of Rho-kinase and Its Inhibitors in Pulmonary Hypertension," *Pharmacol Ther.*, 137(3):352-64, Elsevier, Netherlands (2013).
Fernandes, L.B., et al., "Rho-kinase as a therapeutic target in the treatment of asthma and chronic obstructive pulmonary disease," *Ther Adv Respir Dis.*, 1(1):25-33, SAGE Publishings, United States (2007).

(Continued)

*Primary Examiner* — Doan T Phan
(74) *Attorney, Agent, or Firm* — Sterne, Kessler, Goldstein & Fox P.L.L.C.

(57) ABSTRACT

The invention relates to compounds of formula (I) inhibiting Rho Kinase that are oxidazole derivatives, processes for preparing such compounds, pharmaceutical compositions containing them and therapeutic use thereof. Particularly the compounds of the invention may be useful in the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH).

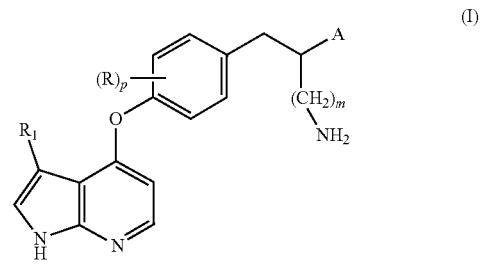

(I)

23 Claims, No Drawings

(56) References Cited

OTHER PUBLICATIONS

Gosens, R., et al., "Rho-kinase as a Drug Target for the Treatment of Airway Hyperrespon-Siveness in Asthma," *Mini-Rev. Med. Chem.*, 2006, 6(3):339-348, Bentham Science Publishers, United Arab Emirates (2006).

International Search Report and Written Opinion for International Application No. PCT/EP2018/084548, European Patent Office, Netherlands, dated Mar. 7, 2019, 8 pages.

Jiang, C., et al., "Fasudil, a Rho-Kinase Inhibitor, Attenuates Bleomycin-Induced Pulmonary Fibrosis in Mice," *Int. J. Mol. Sci.*, 13(7):8293-8307, MDPI, Switzerland (2012).

Riento, K. and Ridley, A. J., "Rocks: Multifunctional Kinases in Cell Behavior," *Nat. Rev. Mol. Cell Biol.*, 4(6), 446-456, Springer Nature Limited, Germany (2003).

\* cited by examiner

OXADIAZOLE DERIVATIVES AS RHO-KINASE INHIBITORS

FIELD OF THE INVENTION

The present invention relates to compounds inhibiting Rho Kinase (hereinafter ROCK Inhibitors); particularly the invention relates oxadiazole derivatives, processes for preparing such compounds, pharmaceutical compositions containing them and therapeutic use thereof.

The compounds of the invention are inhibitors of the activity or function of the ROCK-I and/or ROCK-II isoforms of the Rho-associated coiled-coil forming protein kinase (ROCK).

Therefore, the compounds of the invention may be useful in the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH).

BACKGROUND OF THE INVENTION

Rho-associated coiled-coil forming protein kinase (ROCK) belongs to the AGC (PKA/PKG/PKC) family of serine-threonine kinases. Two human isoforms of ROCK have been described. ROCK-I (also referred to as p160 ROCK or ROCKβ) and ROCK-II (ROCKα) are approximately 160 kDa proteins containing an N-terminal Ser/Thr kinase domain, followed by a coiled-coil structure, a pleckstrin homology domain, and a cysteine-rich region at the C-terminus (Riento, K.; Ridley, A. J. Rocks: multifunctional kinases in cell behaviour. Nat. Rev. Mol. Cell Biol. 2003, 4, 446-456).

Both ROCK-II and ROCK-I are expressed in many human and rodent tissues including the heart, pancreas, lung, liver, skeletal muscle, kidney and brain (Riento and Ridley, 2003). In patients with pulmonary hypertension, ROCK activity is significantly higher in both lung tissues and circulating neutrophils as compared with controls (Duong-Quy S, Bei Y, Liu Z, Dinh-Xuan AT. Role of Rho-kinase and its inhibitors in pulmonary hypertension. Pharmacol Ther. 2013; 137(3):352-64). A significant correlation was established between neutrophil ROCK activity and the severity and duration of pulmonary hypertension (Duong-Quy et al., 2013).

There is now substantial evidence that ROCK is involved in many of the pathways that contribute to the pathologies associated with several acute and chronic pulmonary diseases, including asthma, COPD, bronchiectasis and ARDS/ALI. Given the biological effect of ROCK, selective inhibitors have the potential to treat a number of pathological mechanisms in respiratory diseases, such as smooth muscle hyper-reactivity, bronchoconstriction, airway inflammation and airway remodeling, neuromodulation and exacerbations due to respiratory tract viral infection (Fernandes L B, Henry P J, Goldie R G. Rho kinase as a therapeutic target in the treatment of asthma and chronic obstructive pulmonary disease. Ther Adv Respir Dis. 2007 October; 1(1):25-33). Indeed the Rho kinase inhibitor Y-27632 causes bronchodilatation and reduces pulmonary eosinophilia trafficking and airways hyperresponsiveness (Gosens, R.; Schaafsma, D.; Nelemans, S. A.; Halayko, A. J. Rhokinase as a drug target for the treatment of airway hyperresponsiveness in asthma. Mini-Rev. Med. Chem. 2006, 6, 339-348). Pulmonary ROCK activation has been demonstrated in humans with idiopathic pulmonary fibrosis (IPF) and in animal models of this disease. ROCK inhibitors can prevent fibrosis in these models, and more importantly, induce the regression of already established fibrosis, thus indicating ROCK inhibitors as potential powerful pharmacological agents to halt progression of pulmonary fibrosis (Jiang, C.; Huang, H.; Liu, J.; Wang, Y.; Lu, Z.; Xu, Z. Fasudil, a rho-kinase inhibitor, attenuates bleomycin-induced pulmonary fibrosis in mice. Int. J. Mol. Sci. 2012, 13, 8293-8307).

Various compounds have been described in the literature as Rho Kinase Inhibitors. See e.g. WO2004/039796; WO2006/009889; WO2010/032875; WO2009/079008; WO2014/118133, and from the same Applicant WO 2018/115383 and WO 2018/138293.

There remains a potential for developing novel and pharmacologically improved ROCK inhibitors in many therapeutic areas such as: cardiovascular and respiratory diseases, erectile dysfunction, fibrotic diseases, insulin resistance, kidney failure, central nervous system disorders, auto-immune diseases and oncology.

In view of the number of pathological responses which are mediated by ROCK enzymes, there is a continuing need for inhibitors of such enzymes which can be useful in the treatment of many disorders. The present invention relates to novel compounds which are inhibitors of ROCK-I and ROCK-II isoforms of the Rho-associated coiled-coil forming protein kinase (ROCK)), as demonstrated by the pharmacological activity data reported. Furthermore the compounds of the invention have therapeutically desirable characteristics, that makes them particularly suitable to be administered also by inhalation for the treatment of respiratory disease. The compounds of the invention are particularly promising for some pulmonary diseases including asthma, chronic obstructive pulmonary disease (COPD), idiopathic pulmonary fibrosis (IPF) and pulmonary hypertension (PH) and specifically pulmonary arterial hypertension (PAH).

SUMMARY OF THE INVENTION

The present invention is directed to compounds of formula I

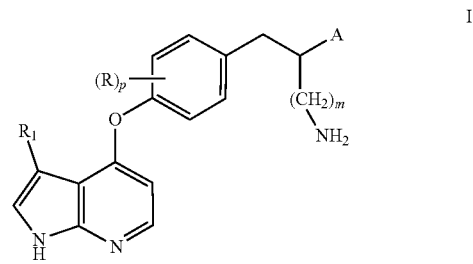

wherein R, $R_1$, A, p and m are as reported below in the detailed description of the invention, acting as ROCK inhibitors, to processes for the preparation thereof, pharmaceutical compositions comprising them either alone or in combination with one or more active ingredient, in admixture with one or more pharmaceutically acceptable carrier.

In one aspect, the invention provides the use of a compound of formula I for the manufacture of a medicament.

In a further aspect, the invention provides the use of a compound of formula I for the preparation of a medicament for the treatment of any disease characterized by ROCK enzyme aberrant activity and/or wherein an inhibition of activity is desirable and in particular through the selective inhibition of the ROCK enzyme isoforms over other Kinases.

Moreover the invention provides a method for prevention and/or treatment of any disease wherein a ROCK enzyme inhibition is desirable, said method comprises administering to a patient in need of such treatment a therapeutically effective amount of a compound of formula I.

In particular the compounds of the invention alone or combined with other active ingredients may be administered for the prevention and/or treatment of a pulmonary disease including asthma, chronic obstructive pulmonary disease (COPD), idiopathic pulmonary fibrosis (IPF) and pulmonary hypertension (PH) and specifically pulmonary arterial hypertension (PAH).

DETAILED DESCRIPTION OF THE INVENTION

The invention relates to compounds of formula I

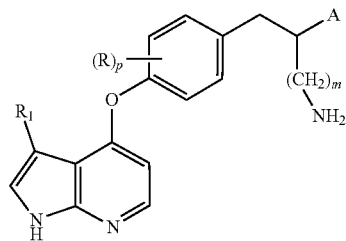

wherein
p is zero or an integer from 1 to 3;
m is zero or an integer from 1 to 2;
A is an oxadiazole ring further substituted by $R_2$;
each R, when present, is an halogen;
$R_1$ is selected from the group consisting of:
—H,
halogen,
—CN,
$(C_1-C_6)$ alkyl,
$R_2$ is selected from the group consisting of:
—H,
$(C_1-C_6)$ alkyl,
$(C_1-C_6)$ haloalkyl,
$(C_1-C_6)$ hydroxyalkyl,
$(C_1-C_6)$ aminoalkyl,
$(C_1-C_6)$ alkoxy $(C_1-C_6)$ alkyl,
aryl,
heteroaryl,
aryl$(C_1-C_6)$alkyl,
each of said aryl, heteroaryl is further optionally substituted by one or more group selected independently from halogen, —CN, —OH, $(C_1-C_8)$alkyl, $(C_1-C_6)$ haloalkyl, $(C_1-C_{10})$alkoxy, aryl, aryl$(C_1-C_6)$alkyl, carbamoyl, $(C_1-C_6)$ aminoalkyl, $(C_1-C_6)$ hydroxyalkyl, or pharmaceutically acceptable salts and solvates thereof.
Definitions The term "pharmaceutically acceptable salts" refers to derivatives of compounds of formula I wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "halogen" or "halogen atoms" includes fluorine, chlorine, bromine, and iodine atom, preferably chlorine or fluorine.

The term "$(C_1-C_6)$ alkyl" refers to straight-chained or branched alkyl groups wherein the number of carbon atoms is in the range 1 to 6. Particular alkyl groups are methyl, ethyl, n-propyl, isopropyl and t-butyl.

The expressions "$(C_1-C_6)$ haloalkyl" refer to the above defined "$(C_1-C_6)$alkyl" groups wherein one or more hydrogen atoms are replaced by one or more halogen atoms, which can be the same or different.

Examples of said $(C_1-C_6)$ haloalkyl groups may thus include halogenated, poly-halogenated and fully halogenated alkyl groups wherein all of the hydrogen atoms are replaced by halogen atoms, e.g. trifluoromethyl or difluoro methyl groups.

By way of analogy, the terms "$(C_1-C_6)$ hydroxyalkyl" or "$(C_1-C_6)$ aminoalkyl" refer to the above defined "$(C_1-C_6)$ alkyl" groups wherein one or more hydrogen atoms are replaced by one or more hydroxy (OH) or amino group respectively. Examples include respectively hydroxymethyl, aminomethyl, dimethylaminopropyl and the like.

In the present description, unless otherwise provided, the definition of aminoalkyl encompasses alkyl groups (i.e. "$(C_1-C_6)$ alkyl" groups) substituted by one or more amino group ($NR_7R_8$). Thus, an example of aminoalkyl is a mono-aminoalkyl group such as $R_7R_8N-(C_1-C_6)$ alkyl.

With reference to the substituent $R_7$ and $R_8$ as defined above and below, when $R_7$ and $R_8$ are taken together with the nitrogen atom they are linked to form a 4 to 6 membered heterocyclic radical, at least one further ring carbon atom in the said heterocyclic radical is optionally replaced by at least one heteroatom (e.g. N, S or O) and/or may bear-oxo (=O) substituent groups. It is understood that the said heterocyclic radical might be further optionally substituted on any available position in the ring, namely on a carbon atom, or on any heteroatom available for substitution. Substitution on a carbon atom includes spiro disubstitution as well as substitution on two adjacent carbon atoms, in both cases thus form an additional 5 to 6 membered heterocyclic ring. Examples of said heterocycle radicals are 1-pyrrolidinyl, 1-piperidinyl, 1-piperazinyl, 4-morpholinyl, piperazin-4yl-2-one, 4-methylpiperazine-1-yl, 4-metylpiperazine-1-yl-2-one, 7-methyl-2,7-diazaspiro [3.5]nonan-2-yl, 2-methyl-2,9-diazaspiro [5.5]undecan-9-yl, 9-methyl-3,9-diazaspiro [5.5]undecan-3-yl, (3aR,6aS)-5-methyl-octahydropyrrolo [3,4-c]pyrrol-2-yl, 8-methyl-2,8-diazaspiro [4.5]decane-2-yl, 5-methyloctahydropyrrolo [3,4-c]pyrrole-2-yl, 1,1-dioxidothiomorpholin-4yl.

The term "$(C_3-C_{10})$ cycloalkyl" likewise "$(C_3-C_6)$ cycloalkyl" refers to saturated cyclic hydrocarbon groups containing the indicated number of ring carbon atoms.

Examples include cyclopropyl, cyclobutyl, cyclopentyl, cyclohexyl, cycloheptyl, and polycyclic ring systems such as adamantan-yl.

The term "$(C_2-C_6)$ alkenyl" refers to straight or branched carbon chains with one or more double bonds, conjugated or not conjugated, in cis or trans configuration, wherein the number atoms is in the range 2 to 6.

By way of analogy, the terms "$(C_5-C_7)$ cycloalkenyl" refers to cyclic hydrocarbon groups containing from 5 to 7 ring carbon atoms and one or two double bonds.

The term "$(C_2-C_6)$ alkynyl" refers to straight or branched carbon chains with one or more triple bonds wherein the number atoms is in the range 2 to 6.

The term "$(C_2-C_6)$ hydroxyalkynyl" refers to the above defined "$(C_1-C_6)$ alkynyl" groups wherein one or more hydrogen atoms are replaced by one or more hydroxy (OH) group.

The term "$(C_2-C_6)$ aminoalkynyl" refers to the above defined "$(C_1-C_6)$ alkynyl" groups wherein one or more hydrogen atoms are replaced by one or more ($—NR_7R_8$) groups.

The expression "aryl" refers to mono, bi- or tri-cyclic carbon ring systems which have 6 to 20, preferably from 6 to 15 ring atoms, wherein at least one ring is aromatic. The expression "heteroaryl" refers to mono-, bi- or tri-cyclic ring systems with 5 to 20, preferably from 5 to 15 ring atoms, in which at least one ring is aromatic and in which at least one ring atom is a heteroatom (e.g. N, S or O).

Examples of suitable aryl or heteroaryl monocyclic ring systems include, for instance, phenyl, thienyl, pyrrolyl, pyrazolyl, imidazolyl, isoxazolyl, oxazolyl, isothiazolyl, thiazolyl, pyridinyl, pyrimidinyl, pyrazinyl, triazinyl, furanyl radicals and the like.

Examples of suitable aryl or heteroaryl bicyclic ring systems include naphthalenyl, biphenylenyl, purinyl, pteridinyl, pyrazolopyrimidinyl, benzotriazolyl, benzoimidazole-yl, quinolinyl, isoquinolinyl, indolyl, isoindolyl, benzothiopheneyl, benzodioxinyl, dihydrobenzodioxinyl, indenyl, dihydro-indenyl, dihydrobenzo[1,4]dioxinyl, benzothiazole-2-yl, dihydrobenzodioxepinyl, benzooxazinyl radicals and the like.

Examples of suitable aryl or heteroaryl tricyclic ring systems include fluorenyl radicals as well as benzocondensed derivatives of the aforementioned heteroaryl bicyclic ring systems.

In an analogous manner, the expressions "arylene" and "heteroarylene" refer to divalent groups, such a phenylene, biphenylene and thienylene. Such groups are also commonly named as "arenediyl" or "heteroarenediyl" groups. For example o-phenylene is also named benzene-1,2-diyl. Thienyl-ene is alternatively named thiophenediyl.

The expression "$(C_3-C_6)$ heterocycloalkyl" refers to saturated or partially unsaturated monocyclic $(C_3-C_6)$ cycloalkyl groups in which at least one ring carbon atom is replaced by at least one heteroatom (e.g. N, S or O) or may bear an -oxo (=O) substituent group. Said heterocycloalkyl (i.e. heterocyclic radical or group) may be further optionally substituted on the available positions in the ring, namely on a carbon atom, or on an heteroatom available for substitution. Substitution on a carbon atom includes spiro disubstitution as well as substitution on two adjacent carbon atoms, in both cases thus form additional condensed 5 to 6 membered heterocyclic ring. Examples of $(C_3-C_6)$ heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, dihydroisoxazolyl, pyrrolidin-2-one-yl, dihydropyrrolyl radicals and the like.

Specific examples of said heterocycle radicals are 1-pyrrolidinyl, 1-methyl-2-pyrrolidinyl, 1-piperidinyl, 1-piperazinyl, 4-morpholinyl, piperazin-4yl-2-one, 4-methylpiperazine-1-yl, 1-methylpiperidin-4yl, 4-metylpiperazine-1-yl-2-one, 7-methyl-2,7-diazaspiro [3.5]nonan-2-yl, 2-methyl-2, 9-diazaspiro [5.5]undecan-9-yl, 9-methyl-3,9-diazaspiro [5.5]undecan-3-yl, and (3aR,6aS)-5-methyl-octahydropyrrolo [3,4-c]pyrrol-2-yl.

The term "aryl $(C_1-C_6)$ alkyl" refers to an aryl ring linked to a straight-chained or branched alkyl groups wherein the number of carbon atoms is from 1 to 6, e.g. phenylmethyl (i.e. benzyl), phenylethyl or phenylpropyl.

Likewise the term "heteroaryl $(C_1-C_6)$ alkyl" refers to an heteroaryl ring linked to a straight-chained or branched alkyl groups wherein the number of carbon atoms is from 1 to 6, e.g. furanylmethyl.

The term "alkanoyl", refers to HC(O)— or to alkylcarbonyl groups (e.g. $(C_1-C_6)$alkylC(O)— wherein the group "alkyl" has the meaning above defined. Examples include formyl, acetyl, propanoyl, butanoyl.

Likewise "$(C_1-C_6)$alkyl-sulfonyl" refers to a "$(C_1-C_6)$ alkyl-S(O)$_2$ group wherein alkyl has the meaning above defined. An example is represented by methylsulfonyl.

The term "carbamoyl" refers to amino carbonyl derived groups —C(O)NR$_7$R$_8$, wherein R$_7$ and R$_8$ are as defined above in the definition of aminoalkyl groups and including substituted (preferred aminoalkyl substituted) and spiro substituted derivatives. Examples of such carbamoyl groups include aminocarbonyl, piperazine-1-carbonyl, morpholine-N-carbonyl, morpholine-N-carbonyl, N-(2-(dimethylamino) ethyl)aminocarbonyl, N-(2-(dimethylamino)ethyl)-N-methylaminocarbonyl, N-(3-(dimethylamino)propyl)-N-methylamino carbonyl, 4-methylpiperazine-1-carbonyl, 4-(dimethylamino)piperidin-1-carbonyl, N-(2-(4-methylpiperazin-1-yl)ethyl)aminocarbonyl, (2-morpholinoethyl) aminocarbonyl, N-methyl-N-(2-morpholino-ethyl) aminocarbonyl, N-(2-(piperidin-1-yl)ethyl)aminocarbonyl, N-methyl-N-(2-(piperidin-1-yl)ethyl)aminocarbonyl, N-(1-methylpiperidin-4-yl-methyl) aminocarbonyl, N-methyl-N-(1-methylpiperidin-4-yl)aminocarbonyl, N-methyl-N-(1-methylpiperidin-4-yl)aminocarbonyl, 5-methyloctahydropyrrolo [3,4-c]pyrrole-2 carbonyl.

The term "hydroxycarbonyl" refers to a terminal group HOC(O)—.

The term "$(C_1-C_{10})$ alkoxy" or "$(C_1-C_{10})$ alkoxyl", likewise "$(C_1-C_6)$ alkoxy" or "$(C_1-C_6)$ alkoxyl" etc., refers to a straight or branched hydrocarbon of the indicated number of carbons, attached to the rest of the molecule through an oxygen bridge. Likewise "$(C_1-C_6)$alkylthio" refers to the above hydrocarbon attached through a sulfur bridge.

The expression "$(C_1-C_6)$ haloalkoxy" or "$(C_1-C_6)$ haloalkoxyl" refers to the above defined haloalkyl, attached through an oxygen bridge, e.g. trifluoromethoxy.

By analogy, the expressions "$(C_3-C_6)$ heterocycloalkyloxyl" and "$(C_3-C_6)$ heterocycloalkyl $(C_1-C_6)$ alkoxyl" refer to heterocycloalkyl groups attached through an oxygen bridge and chained heterocycloalkyl-alkoxyl groups respectively. Examples of such $(C_3-C_6)$ heterocycloalkyloxyl and $(C_3-C_6)$ heterocycloalkyl $(C_1-C_6)$ alkoxyl groups are respectively (piperidin-4-yl)oxy, 1-methylpiperidin-4-yl)oxy, 2-(piperidin-4-yl)ethoxyl, 2-(1-methylpiperidin-4-yl) ethoxy, and 2-(4-morpholino)ethoxy.

The expressions "Aryloxyl" and "Aryl $(C_1-C_6)$ alkoxyl" likewise "heteroAryloxyl" and "Heteroaryl $(C_1-C_6)$ alkoxyl" refer to Aryl or Heteroaryl groups attached through an oxygen bridge and chained Aryl-alkoxyl or HeteroAryl-alkoxyl groups. Examples of such groups are phenyloxy, benzyloxy and pyridinyloxy respectively.

Likewise, the expressions "($C_3$-$C_6$) heterocycloalkyl-($C_1$-$C_6$) alkyl" and "($C_3$-$C_6$) cycloalkyl-($C_1$-$C_6$) alkyl" refer to the above defined heterocycloalkyl and cycloalkyl groups attached to the rest of the molecule via an alkyl group of the indicated number of carbons. Examples include piperidin-4-yl-methyl and cyclohexylethyl.

The expression "($C_1$-$C_6$) alkoxy-($C_1$-$C_6$) alkyl" refers to the above defined alkoxy group attached to the rest of the molecule via an alkyl group of the indicated number of carbons. Examples include methoxymethyl and methoxypropyl.

The expression "($C_1$-$C_6$) alkoxycarbonyl" refers to the above defined alkoxy group attached to the rest of the molecule via a carbonyl group, e.g. ethoxycarbonyl.

The expression like "($C_1$-$C_6$) alkoxycarbonyl-amino" refers to the above defined alkoxy group attached to the rest of the molecule via a carbonyl group followed by an amino group (—$NR_7$—), e.g. tert-butoxy-carbonyl-amino-.

"($C_1$-$C_6$) alkoxycarbonyl ($C_3$-$C_6$) heterocycloalkyl ($C_1$-$C_6$) alkyl" refers to alkoxy carbonyl heterocycloalkyl substituents enchained in the said order and attached to the rest of the molecule via an alkyl group of the indicated number of carbons, e.g. (tert-butyl piperidine-1-carboxylate)-4 yl-methyl.

The expression "($C_1$-$C_6$) aminoalkoxyl" refers to ($C_1$-$C_6$) aminoalkyl groups as defined above attached through an oxygen bridge, e.g. (2-(dimethylamino)ethoxy.

The expression "($C_1$-$C_6$) hydroxyalkoxyl" refers to hydroxyalkyl groups as defined above attached to the rest of the molecule through an oxygen bridge, e.g. hydroxyethoxy.

The expression "($C_1$-$C_6$) aminoalkylcarbamoyl" refers to a "carbamoyl" group, as defined above, substituted with a ($C_1$-$C_6$) aminoalkyl group (i.e. —C(O)$NR_7R_8$ wherein e.g. $R_8$ is an ($C_1$-$C_6$) aminoalkyl), e.g. 2(dimethylamino) ethyl carbamoyl.

The term "aryl oxyl ($C_1$-$C_6$) alkyl" refers to an aryl-O— wherein aryl has the meaning above defined attached to the rest of the molecule via an alkyl group of the indicated number of carbons, e.g. phenoxyethyl.

The term "aryl alkanoyl" refers to an arylC(O) or arylalkylcarbonyl group [e.g. Aryl($C_1$-$C_6$)alkylC(O)—] wherein aryl and alkyl have the meaning above defined. Examples are represented by benzoyl, phenylacetyl, phenylpropanoyl or phenylbutanoyl radicals. Likewise "aryl sulfonyl" refers to an arylS(O)$_2$ group wherein aryl has the meaning above defined, e.g. phenylsulfonyl.

Likewise, enchained substituents derive their definition from the composing fragments, like in the above reported definitions, such as "($C_3$-$C_6$) cycloalkyl-carbonyl", "($C_3$-$C_6$) heterocycloalkyl-carbonyl", "heteroaryl-carbonyl"; referring to the above defined fragments attached to the rest of the molecule via a carbonyl group. Examples of such groups include cyclopropanecarbonyl, pyrrolidine-3-carbonyl, (pyridin-3-yl)carbonyl.

The expression "saturated, partially unsaturated or aromatic, five or six membered cycloalkane-diyl, arylene-diyl or heterocycle-diyl" refers to suitable disubstituted cycloalkane or heterocycle or aromatic residue with five or six elements including 1,2-, 1,3- or 1,4-benzene-diyl; 2,3-, 3,4-, 4,5- or 5,6-pyridine-diyl; 3,4-, 4,5- or 5,6-pyridazine-diyl; 4,5- or 5,6-pyrimidine-diyl; 2,3-pyrazinediyl; 2,3-, 3,4- or 4,5-thiophene-diyl/furane-diyl/pyrrole-diyl; 4,5-imidazole-diyl/oxazole-diyl/thiazolediyl; 3,4- or 4,5-pyrazole-diyl/isoxazolediyl/isothiazole-diyl their saturated or partially unsaturated analogues and the like. Other non-vicinal disubstituted residues (diradical) are included too, such as 4,6-pyrimidine-diyl, and the like.

The expression "ring system" refers to mono- or bicyclic or polycyclic ring systems which may be saturated, partially unsaturated or unsaturated, such as aryl, ($C_3$-$C_{10}$) cycloalkyl, ($C_3$-$C_6$) heterocycloalkyl or heteroaryl.

The terms "group", "radical" or "fragment" or "substituent" are synonymous and are intended to indicate functional groups or fragments of molecules attachable to a bond or other fragments or molecules. Thus, as an example, a "heterocyclic radical" herein refers to a mono- or bi-cyclic saturated or partially saturated heterocyclic moiety (group, radical), preferably a 4 to 11 membered monocyclic radical, at least one further ring carbon atom in the said heterocyclic radical is optionally replaced by at least one further heteroatom independently selected from N, S or O and/or may bear an -oxo (=O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic ring. Examples of said heterocycle radicals are 1-pyrrolidinyl, 1-piperidinyl, 1-piperazinyl, 4-morpholinyl, piperazin-4-yl-2-one, 4-methylpiperazine-1-yl, 4-metylpiperazine-1-yl-2-one, 7-methyl-2,7-diazaspiro-[3.5]nonan-2-yl, 2-methyl-2,9-diazaspiro [5.5] undecan-9-yl, 9-methyl-3,9-diazaspiro [5.5]-undecan-3-yl, and (3aR,6aS)-5-methyl-octahydropyrrolo [3,4-c]pyrrol-2-yl and the like.

A dash ("-") that is not between two letters or symbols is meant to represent the point of attachment for a substituent. When graphically represented the point of attachment in a cyclic functional group is indicated with a dot ("•") localized in one of the available ring atom where the functional group is attachable to a bond or other fragment of molecules.

An oxo moiety is represented by (O) as an alternative to the other common representation, e.g. (=O). Thus, in terms of general formula, the carbonyl group is herein preferably represented as —C(O)— as an alternative to the other common representations such as —CO—, —(CO)— or —C(=O)—. In general, the bracketed group is a lateral group, not included into the chain, and brackets are used, when deemed useful, to help disambiguating linear chemical formulas; e.g. the sulfonyl group —SO$_2$— might be also represented as —S(O)$_2$— to disambiguate e.g. with respect to the sulfinic group —S(O)O—.

When a numerical index is used like in the statement "p is zero or an integer from 1 to 3" the statement (value) "p is zero" means that the substituent R is absent, that is to say there is no substituent R on the ring.

Whenever basic amino or quaternary ammonium groups are present in the compounds of formula I, physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups such as COOH groups, corresponding physiological cation salts may be present as well, for instance including alkaline or alkaline earth metal ions.

It will be apparent that compounds of formula I when contain one or more stereogenic center, may exist as optical stereoisomers.

Where the compounds of the invention have at least one stereogenic center, they may accordingly exist as enantiomers. Where the compounds according to the invention possess two or more stereogenic centers, they may additionally exist as diastereoisomers. All such single enantiomers, diastereoisomers and mixtures thereof in any proportion are encompassed within the scope of the invention. The absolute configuration (R) or (S) for carbon bearing a stereogenic center is assigned on the basis of Cahn-Ingold-Prelog nomenclature rules based on groups' priorities.

The invention further concerns the corresponding deuterated derivatives of compounds of formula I.

All preferred groups or embodiments described above and herebelow for compounds of formula I may be combined among each other and apply as well mutatis mutandis.

In a preferred embodiment, the invention is directed to compounds of formula (I) as defined above wherein A is an oxidiazole ring selected in the group consisting of

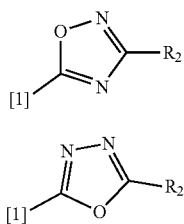

wherein [1] represents the point of attachment of oxadiazole ring to the rest of molecule.

In a second preferred embodiment, the invention is directed to compounds of formula I as defined above

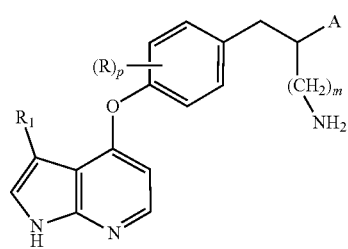

wherein
p is zero or 1;
m is zero or 1;
A is an oxadiazole ring selected in the group consisting of

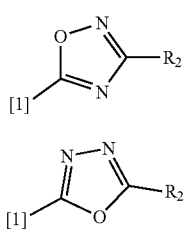

R, when present, is halogen;
R$_1$ is selected from the group consisting of:
—H
(C$_1$-C$_6$) alkyl;

R$_2$ is selected from the group consisting of:
(C$_1$-C$_6$) alkyl,
(C$_1$-C$_6$) aminoalkyl,
(C$_1$-C$_6$) alkoxy (C$_1$-C$_6$) alkyl,
aryl,
heteroaryl,
aryl(C$_1$-C$_6$)alkyl.

In a third preferred embodiment, the invention is directed to compounds of formula (I) as defined above:

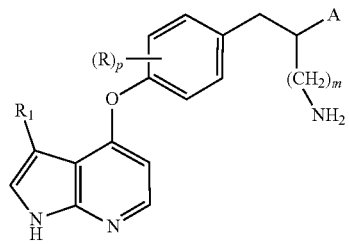

p is zero or 1;
m is zero or 1;
A is an oxadiazole ring selected in the group consisting of

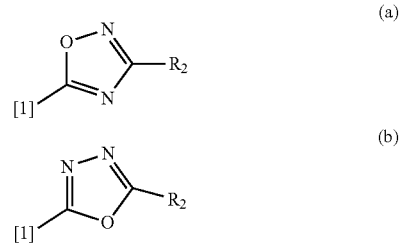

R, when present, is fluorine;
R$_1$ is —H or methyl,
R$_2$ is selected from the group consisting of:
methyl,
dimethylpropanamine,
methoxyethyl,
phenyl,
3-pyridinyl,
phenylethyl and phenylmethyl.

The invention also provides a pharmaceutical composition comprising a compound of formula I or a pharmaceutically acceptable salt thereof in admixture with one or more pharmaceutically acceptable carrier or excipient, either alone or in combination with one or more further active ingredient.

In one aspect, the invention provides a compound of formula I for use as a medicament.

In a further aspect, the invention provides the use of a compound of formula I, or a pharmaceutically acceptable salt thereof, in the manufacture of a medicament for the treatment of disorders associated with ROCK enzymes mechanisms, particularly for the treatment of disorders such as pulmonary diseases.

In particular, the invention provides compounds of formula I for use in the prevention and/or treatment of pulmonary disease selected from the group consisting of asthma, chronic obstructive pulmonary disease COPD, idiopathic pulmonary fibrosis (IPF), pulmonary hypertension (PH) and specifically Pulmonary Arterial Hypertension (PAH).

The invention also provides a method for the prevention and/or treatment of disorders associated with ROCK enzymes mechanisms, said method comprising administering to a patient in need of such treatment a therapeutically effective amount of a compound of formula I.

In particular the invention provides methods for the prevention and/or treatment wherein the disorder is asthma, chronic obstructive pulmonary disease COPD idiopathic pulmonary fibrosis (IPF), Pulmonary hypertension (PH) and specifically Pulmonary Arterial Hypertension (PAH).

According to specific embodiments, the invention provides the compounds listed in the table 1 below and pharmaceutical acceptable salts thereof.

TABLE 1

| Ex. N. | Chemical Name |
|---|---|
| 1 | (S)-2-(3-fluoro-4-((3-methyl-1H-pyrrolo[2,3-b]pyridin-4-yl)oxy)phenyl)-1-(3-phenyl-1,2,4-oxadiazol-5-yl)ethanamine |
| 2 | (S)-2-(3-fluoro-4-((3-methyl-1H-pyrrolo[2,3-b]pyridin-4-yl)oxy)phenyl)-1-(3-(2-methoxyethyl)-1,2,4-oxadiazol-5-yl)ethanamine |
| 3 | (S)-2-(3-fluoro-4-((3-methyl-1H-pyrrolo[2,3-b]pyridin-4-yl)oxy)phenyl)-1-(3-methyl-1,2,4-oxadiazol-5-yl)ethanamine |
| 4 | (S)-2-(3-fluoro-4-((3-methyl-1H-pyrrolo[2,3-b]pyridin-4-yl)oxy)phenyl)-1-(3-phenethyl-1,2,4-oxadiazol-5-yl)ethanamine |
| 5 | (S)-2-(3-fluoro-4-((3-methyl-1H-pyrrolo[2,3-b]pyridin-4-yl)oxy)phenyl)-1-(3-(pyridin-3-yl)-1,2,4-oxadiazol-5-yl)ethanamine |
| 6 | (S)-3-(5-(1-amino-2-(3-fluoro-4-((3-methyl-1H-pyrrolo[2,3-b]pyridin-4-yl)oxy)phenyl)ethyl)-1,2,4-oxadiazol-3-yl)-N,N-dimethylpropan-1-amine |
| 7 | (S)-2-(4-((1H-pyrrolo[2,3-b]pyridin-4-yl)oxy)phenyl)-1-(3-phenyl-1,2,4-oxadiazol-5-yl)ethanamine |
| 8 | 3-(3-fluoro-4-((3-methyl-1H-pyrrolo[2,3-b]pyridin-4-yl)oxy)phenyl)-2-(3-phenethyl-1,2,4-oxadiazol-5-yl)propan-1-amine |
| 9 | (S)-1-(5-benzyl-1,3,4-oxadiazol-2-yl)-2-(3-fluoro-4-((3-methyl-1H-pyrrolo[2,3-b]pyridin-4-yl)oxy)phenyl)ethanamine |

The compounds of the invention, including all the compounds here above listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the invention can be obtained using the processes described herein or by using other known methods, reagents and starting materials. When typical or preferred process conditions (i.e. reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by those skilled in the art by routine optimization procedures.

Thus, processes described below and reported in the following schemes should not be viewed as limiting the scope of the synthetic processes available for the preparation of the compounds of the invention.

In some cases, generally known protective groups (PG) could be employed when needed to mask or protect sensitive or reactive moieties, in accordance to general principles of chemistry (Protective group in organic syntheses, 3rd ed. T. W. Greene, P. G. M. Wuts).

The compounds of formula I, including all the compounds here above listed, can be generally prepared according to the procedures shown in the schemes below. Where a specific synthetic step differs from what is described in the general schemes, it has been detailed in the specific examples, and/or in additional schemes.

Compounds of formula I (wherein m is 0 or 1 and A is an oxadiazole ring further substituted by R2) contain at least one stereogenic centre, as marked by an asterisk * in the picture below.

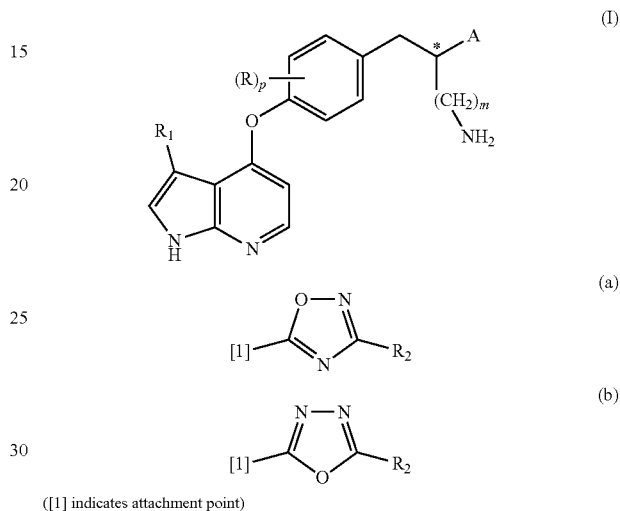

([1] indicates attachment point)

Enantiomerically pure compounds can be prepared according to the reactions described below, by means of enantiomerically pure starting materials and intermediates. Preparation of enantiomerically pure compounds of formula I may be accomplished by means of enantiomerically pure intermediates IV and VIIa or VIIb as found in the following schemes. These intermediates may be commercially available or readily prepared from commercial sources by those of ordinary skill in the art. Optical purity of stereogenic center of reagents is generally retained during the synthesis with an ee equal or greater than 90%. In some cases optical purity may be partially lost with an ee less than 90%. For the sake of graphical representation these examples are reported with the stereochemistry of the most abundant enantiomer and should be considered with their ee % explicitated in experimental procedures.

In another approach, enantiomerically pure compounds can be obtained from the corresponding racemates by means of chiral chromatography. Whenever, in compounds of formula I, there are two or more stereogenic centres, the structure is then characterized by different stereoisomers. Stereochemically pure compounds may be obtained by chiral separation from a diastereoisomeric mixture, or stepwise by chromatographic separation of diastereoisomers followed by further chiral separation into single stereoisomers.

Compounds of formula I may be prepared according to SCHEME 1 as described hereinafter providing at least one synthetic route for the preparation of all examples.

Scheme 1

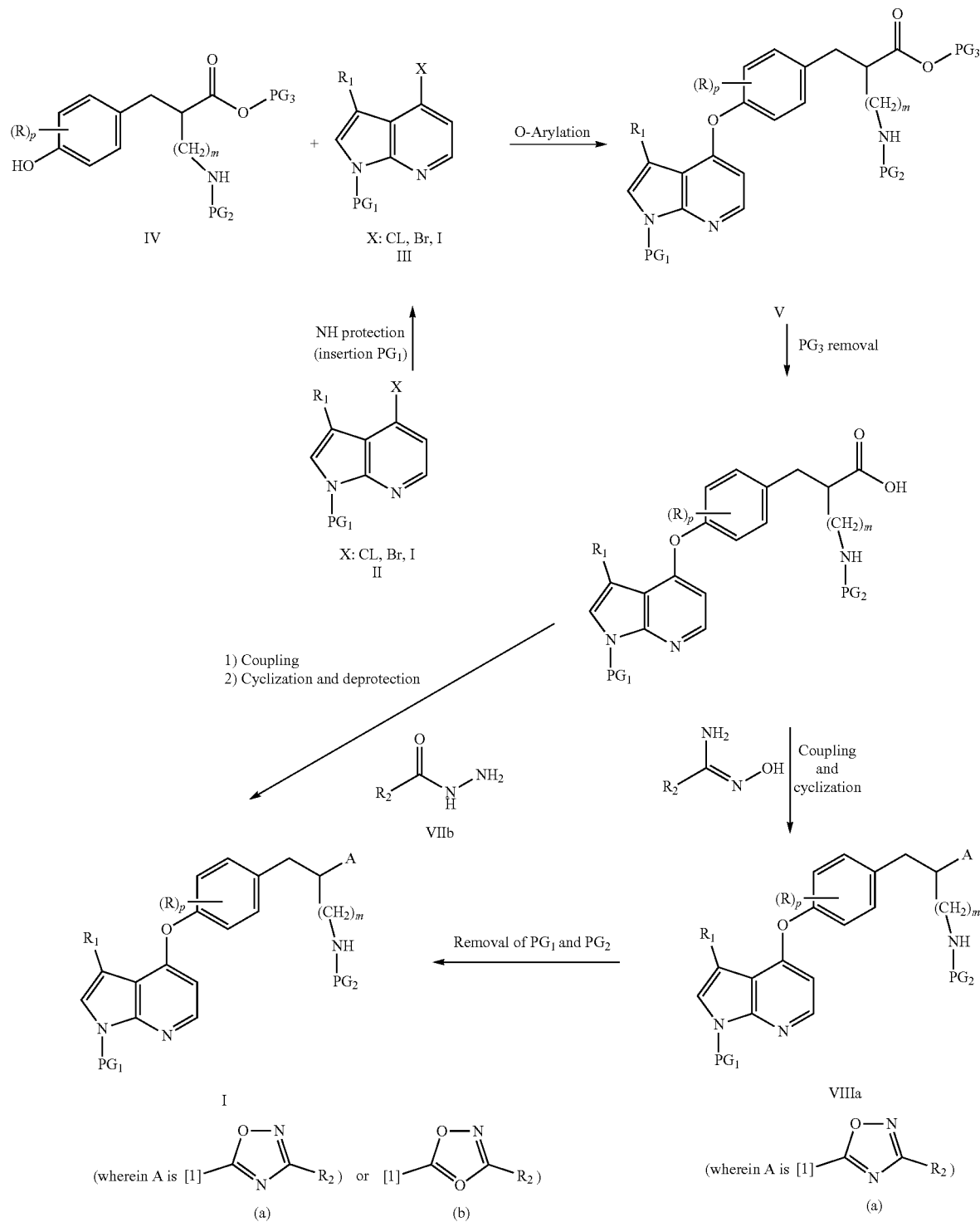

Typical protective groups (PG$_1$) for protection of the NH of the 5-membered ring of the bicyclic intermediate III can be 2-[(trimethylsilyl)ethoxy]methyl (SEM), 4-toluenesulfonyl (Ts) and p-methoxybenzyl (PMB), and anyhow not limiting the use of other protective groups. Intermediate III, wherein PG$_1$ is SEM may be prepared from the corresponding intermediate II and a suitable reagent such as SEM-Cl ([2-(trimethylsilyl)ethoxy]methyl chloride). Reaction between said components may be carried out in a polar organic solvent such as DMF or DCM, in the presence of a strong base, such as NaH, at RT or lower.

The amino group of intermediate IV may be suitably protected as a carbamate with PG$_2$ (for example a Boc group) and the carboxylic acid as an ester with PG$_3$ (for example as the methyl ester or ethyl ester). These transformations may be achieved by using generally well known methods starting from commercially available unprotected amino acid derivatives (Protective group in organic syntheses, 3rd ed. T. W. Greene, P. G. M. Wuts).

According to SCHEME 1, intermediate V may be obtained from Intermediates III and IV through a palladium catalyzed O-arylation. For example, the reaction may be carried out by reacting the aryl halide intermediate III and the phenol derivative IV in a suitable organic solvent such as toluene or THF, in the presence of an inorganic base such as $K_2CO_3$, with a suitable palladium catalytic system such as $Pd_2dba_3$/XPhos or another palladium source/phosphine based ligand at high temperature (around 100° C.) for a few hours (3-6 hours).

Removal of $PG_3$ (when $PG_3$ is a methyl or ethyl) from intermediate V to give the intermediate VI, may be carried out by hydrolysis using an inorganic base such as LiOH in a mixture of organic solvents such as THF or methanol and water, usually at RT and for a time ranging from 10 min to overnight.

Intermediate VIIIa may be obtained by coupling of acid intermediate VI and corresponding N'-hydroxyimidamide VIIa followed by cyclization to form the corresponding 1,2,4-oxadiazole. For example, the coupling reaction may be performed by reacting intermediate VI and VIIa in the presence of an activating agent such as COMU or HATU, with an organic base such as DIPEA or TEA, in an organic solvent such as DCM or THF at temperature usually around RT for time up to overnight, followed by one-pot cyclization in a high boiling organic solvent such as toluene at a temperature around 120° C. for 1-3 hours. Removal of all protective groups from intermediate VIIIa ($PG_1$ and $PG_2$) to give compounds of formula I (wherein A contains an 1,2,4-oxadiazole), may be achieved using generally know methods (Protective group in organic syntheses, 3rd ed. T. W. Greene, P. G. M. Wuts). For example, when $PG_1$ is SEM and $PG_2$ is a Boc groups, cleavage may be achieved by an acidic treatment using TFA in an organic solvent such as DCM or inorganic acids in organic solvents such as hydrochloric acid in dioxane.

Compound of formula I (wherein A contains an 1,3,4-oxadiazole) may be obtained by a two-step process composed by coupling of acid intermediate VI and corresponding hydrazide VIIb to form the corresponding N,N'-diacylhydrazide, followed by a second step of cyclization to build the expected 1,3,4-oxadiazole and concurrent removal of protective groups $PG_1$ and $PG_2$. For example, the coupling reaction may be performed by reacting intermediate VI and VIIb in the presence of an activating agent such as EDC or DCC and HOBt, in an organic solvent such as DMF or NMP, at temperature usually around RT for a time up to overnight. The corresponding N,N'-diacylhydrazine intermediate may be dehydrated in the presence of an appropriate dehydrating agent/base couple such as p-toluenesulfonyl chloride/PS-BEMP in an organic solvent such as THF, followed by an acidic treatment with TFA for a couple of hours. In these conditions, $PG_1$ and $PG_2$ may be consequently removed to give compounds of formula I (wherein A contains an 1,3,4-oxadiazole).

The compounds of the invention are inhibitors of kinase activity, in particular Rho-kinase activity. Generally speaking, compounds which are ROCK inhibitors may be useful in the treatment of many disorders associated with ROCK enzymes mechanisms.

In one embodiment, the disorders that can be treated by the compounds of the present invention include glaucoma, inflammatory bowel disease (IBD) and pulmonary diseases selected from asthma, chronic obstructive pulmonary disease (COPD), interstitial lung disease such as idiopathic pulmonary fibrosis (IPF) and pulmonary arterial hypertension (PAH).

In another embodiment, the disorder that can be treated by the compounds of the present invention is selected from the group consisting of asthma, chronic obstructive pulmonary disease (COPD) and interstitial lung disease such as idiopathic pulmonary fibrosis (IPF) and pulmonary arterial hypertension (PAH).

In a further embodiment, the disorder is selected from idiopathic pulmonary fibrosis (IPF) and pulmonary arterial hypertension (PAH).

The methods of treatment of the invention comprise administering a safe and effective amount of a compound of formula (I) or a pharmaceutically acceptable salt thereof to a patient in need thereof. As used herein, "safe and effective amount" in reference to a compound of formula I or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula I or pharmaceutically acceptable salts thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula I in admixture with one or more pharmaceutically acceptable carrier or excipient, for example those described in Remington's Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds of the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, usually non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention can be administered as the sole active agent or in combination (i.e. as co-therapeutic agents administered in fixed dose combination or in combined therapy of separately formulated active ingredients) with other pharmaceutical active ingredients selected from organic nitrates and NO donors; inhaled NO; stimulator of soluble guanylate cyclase (sGC); prostacyclin analogue PGI2 and agonist of prostacyclin receptors; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors; human neutrophilic elastase inhibitors; compounds inhibiting the signal transduction cascade, such as tyrosine kinase and/or serine/threonine kinase inhibitors; antithrombotic agents, for example platelet aggregation inhibitors, anticoagulants or profibrinolytic substances; active substances for lowering blood pressure, for example calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists; neutral endopeptidase inhibitors; osmotic agents; ENaC blockers; anti-inflammatories including corticosteroids and antagonists of chemokine receptors; bronchodilators for example beta2agonist and muscarinic antagonists; antihistamine drugs; anti-tussive drugs; antibiotics such as macrolide and DNase drug substance and selective cleavage agents such as recombinant human deoxyribonuclease I (rhDNase); agents that inhibit ALK5 and/or ALK4 phosphorylation of Smad2 and Smad3; tryptophan hydroylase 1 (TPH1) inhibitors and multi-kinase inhibitors.

In a preferred embodiment, the compounds of the invention are dosed in combination with phosphodiesterase V such as sildenafil, vardenafil and tadalafil; organic nitrates and NO donors (for example sodium nitroprusside, nitroglycerin, isosorbide mononitrate, isosorbide dinitrate, molsidomine or SIN-1, and inhaled NO); synthetic prostaciclin analogue PGI2 such as iloprost, treprostinil, epoprostenol and beraprost; agonists of prostacyclin receptors such as selexipag and compounds of WO 2012/007539; stimulator of soluble guanylate cyclase (sGC) like riociguat and tyrosine kinase like imatinib, sorafenib and nilotinib and endothelin antagonist (for example macitentan, bosentan, sitaxentan and ambrisentan).

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula I can be administered for example, at a dosage comprised between 0.001 and 1000 mg/day, preferably between 0.1 and 500 mg/day.

When the compounds of formula I are administered by inhalation route, they are preferably given at a dosage comprised between 0.001 and 500 mg/day, preferably between 0.1 and 100 mg/day.

A pharmaceutical composition comprising a compound of the invention suitable to be administered by inhalation, such as inhalable powders, propellant-containing metering aerosols or propellant-free inhalable formulations.

The invention is also directed to a device comprising the pharmaceutical composition comprising a compound according to the invention, which may be a single- or multi-dose dry powder inhaler, a metered dose inhaler and a soft mist nebulizer.

The following examples illustrate the invention.
Preparations of Intermediates and Examples
General Experimental Details Purification by chromatography refers to purification using the CombiFlash® Companion purification system or the Biotage SP1 purification system. Si cartridge refers to an Isolute® SPE Si II cartridge, a pre-packed polypropylene column containing unbonded activated silica with irregular particles with average size of 50 μm and nominal 60 Å porosity. Fractions containing the required product (identified by TLC and/or LCMS analysis) were pooled and concentrated in vacuo. Where an SCX-2 cartridge was used, 'SCX-2 cartridge' refers to an Isolute® pre-packed polypropylene column containing a non-end-capped propylsulphonic acid functionalised silica strong cation exchange sorbent. Where HPLC was used for purification (Purification by MDAP) fractions containing the required product (identified by TLC and/or LCMS analysis) were pooled and the solvent removed using a Biotage EV10 Evaporator. Alternatively the pooled product fraction was lyophilised.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz or on a Bruker Fourier 300 spectrometer with a 5 mm dual probe operating at 300 MHz. Shifts are given in ppm relative to tetramethylsilane.

LC-MS Method 1

Waters Micromass ZQ2000 mass spectrometer with a C18-reverse-phase column (100×2.1 mm Acquity BEH with 1.7 µm particle size) maintained at 40° C., elution with A: water+0.1% formic acid; B: MeCN+0.1% formic acid.
Gradient:

| Gradient — Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionisation method-Electrospray (positive/negative ion).

LC-MS Method 2

Quattro Micro Mass Spectrometer with a C18-reverse-phase column (100×2.1 mm Acquity BEH with 1.7 µm particle size) maintained at 40° C., elution with A: water+0.1% formic acid; B: MeCN+0.1% formic acid.
Gradient:

| Gradient — Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionisation method-Electrospray (positive/negative ion).

LC-MS Method 3

QDa Mass Spectrometer with a C18-reverse-phase column (50×2.1 mm Acquity CSH with 1.7 µm particle size) maintained at 40° C., elution with A: water+0.1% formic acid; B: MeCN+0.1% formic acid.
Gradient:

| Gradient — Time | flow (mL/min) | % A | % B |
|---|---|---|---|
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionisation method-Electrospray (positive/negative ion).

LC-MS Method 4

QDa Mass Spectrometer with a C18-reverse-phase column (50×2.1 mm Acquity BEH with 1.7 µm particle size) maintained at 50° C., elution with A: water+0.1% formic acid; B: MeCN+0.1% formic acid.
Gradient:

| Gradient — Time | flow (mL/min) | % A | % B |
|---|---|---|---|
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionisation method-Electrospray (positive/negative ion).

LC-MS Method 5

Waters Platform LC with a C18-reverse-phase column (30×4.6 mm Phenomenex Luna 3 µm particle size), elution with A: water+0.1% formic acid; B: acetonitrile+0.1% formic acid.
Gradient:

| Gradient — Time | flow (mL/min) | % A | % B |
|---|---|---|---|
| 0.00 | 2 | 95 | 5 |
| 0.50 | 2 | 95 | 5 |
| 4.50 | 2 | 5 | 95 |
| 5.50 | 2 | 5 | 95 |
| 6.00 | 2 | 95 | 5 |

Detection-MS, ELS, UV (100 µl split to MS with in-line UV detector)

MS ionisation method-Electrospray (positive and negative ion).

MDAP Method

Agilent Technologies 1260 Infinity purification system with an XBridge Prep C18 OBD column (19×250 mm, 5 µm OBD) maintained at RT Mobile Phase A: 0.1% aqueous ammonia Mobile Phase B: 0.1% ammonia in acetonitrile Flow Rate: 20 ml/min Gradient Program: 10%-95%, 22 min, centered around a specific focused gradient Sample: Injection of a 20-60 mg/ml solution in DMSO+ optional formic acid and water)

Analytical SFC for Determination of Enantiomeric Excess (ee)

Waters Acquity Qda mass spectrometer with a chiral column, as specified, maintained at 40° C., elution with A: CO2; B: Alcohol+diethylamine.

Using either isocratic conditions or the gradient:

| Gradient — Time | % A | % B |
|---|---|---|
| 0.00 | 95 | 5 |
| 0.50 | 95 | 5 |
| 2.00 | 45 | 55 |
| 4.50 | 45 | 55 |

-continued

| Gradient — Time | % A | % B |
|---|---|---|
| 4.60 | 95 | 5 |
| 5.00 | 95 | 5 |

Detection-UV (210-400 nm), MS

| Chiral method No. | Column | Alcohol | Condition |
|---|---|---|---|
| Chiral method 1 | Diacel Chiralpak IB (100 × 3.0 mm i.d. 3.0 mM) | MeOH | gradient |
| Chiral method 2 | Diacel Chiralpak IC (100 × 3.0 mm i.d. 3.0 mM) | IPA | gradient |
| Chiral method 3 | Diacel Chiralpak IA (100 × 3.0 mm i.d. 3.0 mM) | MeOH | gradient |
| Chiral method 4 | YMC CHIRAL Amylose-C (150 × 5.6 mm i.d. 5.0 mM) | MeOH | Isocratic 25% B |
| Chiral method 5 | YMC CHIRAL Cellulose-C (150 × 4.6 mm i.d. 5.0 mM) | MeOH | isocratic 25% B |

Abbreviations used in the Experimental Section:
COMU=(1-Cyano-2-ethoxy-oxoethylidenaminooxy)dimethylaminomorpholino-carbenium hexafluorophosphate; DCM=Dichloromethane; DIPEA=Di-isopropyl-ethylamine; DMF=N,N-dimethylformamide; DMSO=Dimethylsulphoxide; EDC.HCl=N-(3-Dimethylaminopropyl)-N'-ethylcarbodiimide hydrochloride; h=Hour(s); HOBt=1-Hydroxybenzotriazole; HPLC=High performance liquid chromatography; IPA=Isopropyl alcohol; LCMS=Liquid chromatography-mass spectrometry; MDAP=Mass-directed autopurification; MeCN=Acetonitrile; MeOH=Methanol; Pd2(dba)3=Tris(dibenzylideneacetone)dipalladium(0); PS-BEMP=2-tert-Butylimino-2-diethylamino-1,3-dimethylperhydro-1,3,2-diazaphosphorine, polymer-bound; Rt=Retention time; RT=Room temperature; SFC=Supercritical Fluid Chromatography; TFA=Trifluoroacetic acid; THF=Tetrahydrofuran; XPhos=2-Dicyclohexylphosphino-2',4',6'-triisopropylbiphenyl.

In the procedures that follow, some of the starting materials are identified through an "Intermediate" or "Example" number with indications on step. This is provided merely for assistance to the skilled chemist.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Example 1

Step A

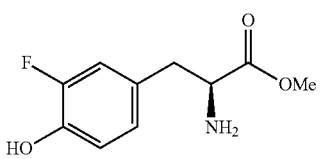 [SMILES: COC(=O)[C@@H](N)Cc1ccc(O)c(F)c1]

Methyl (S)-2-amino-3-(3-fluoro-4-hydroxyphenyl)propanoate (Intermediate 1A-a)

3-Fluoro-L-tyrosine (6.0 g, 30.12 mmol) was suspended in methanol (120 mL) and the mixture was cooled in an ice bath. Thionyl chloride (11 mL, 150.6 mmol) was added dropwise. The mixture was allowed to warm to RT and then stirred overnight. The solvent was evaporated and the residue dissolved in water (50 mL). After basifying the mixture using saturated aqueous sodium hydrogen carbonate, the product was extracted four times with ethyl acetate. The combined organic extracts were dried (Na$_2$SO$_4$) and evaporated to give the desired product as a beige solid (4.55 g).

LCMS (Method 3): Rt=0.65 min, m/z 214.1 [M+H]+

Step B

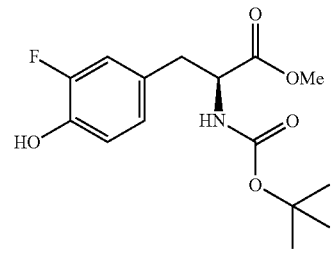 [SMILES: COC(=O)[C@H](Cc1ccc(O)c(F)c1)NC(=O)OC(C)(C)C]

Methyl (S)-2-((tert-butoxycarbonyl)amino)-3-(3-fluoro-4-hydroxyphenyl)-prop-anoate (Intermediate 1B-a)

Intermediate 1A-a (4.55 g, 21.34 mmol) was suspended in a mixture of DCM (153 mL) and THF (77 mL). The mixture was cooled in an ice bath and di-tert-butyl dicarbonate (5.12 g, 23.47 mmol) was added. The reaction mixture was allowed to warm to RT and stirred for 4 h. The solvent was evaporated in vacuo and the crude product was chromatographed on a 120 g Si cartridge eluting with 0-10% 2M methanolic ammonia in DCM. Intermediate 1B-a was obtained as a yellow gum (5.96 g).

LCMS (Method 3): Rt=1.29 min, m/z 336.2 [M+Na]+

Step C

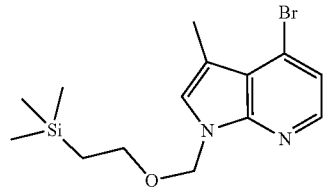 [SMILES: Cc1cn(COCC[Si](C)(C)C)c2nccc(Br)c12]

4-Bromo-3-methyl-14(2-(trimethylsilyl)ethoxy)methyl)-1H-pyrrolo [2,3-b]pyridine (Intermediate 1C-a)

4-Bromo-3-methyl-7-azaindole (4.0 g, 18.95 mmol) was dissolved in DMF (37 mL) and the solution was cooled in an ice bath. Sodium hydride (60% on mineral oil, 1.14 g, 28.43 mmol) was added and the mixture was stirred under a stream of nitrogen for 1 h. 2-(Trimethylsilyl)ethoxymethyl chloride (4.0 mL, 22.74 mmol) was added dropwise and then the reaction mixture was stirred for a further 30 min. After quenching with water (20 mL), the product was extracted three times with ethyl acetate. The combined extracts were dried (Na2SO4) and evaporated. The residue was chromatographed on a 120 g Si cartridge eluting with 0-25% ethyl acetate in cyclohexane to give Intermediate 1C-a as a colourless oil (3.78 g).

LCMS (Method 4): Rt=1.90 min, m/z 341.1/343.0 [M+H]+

Step D

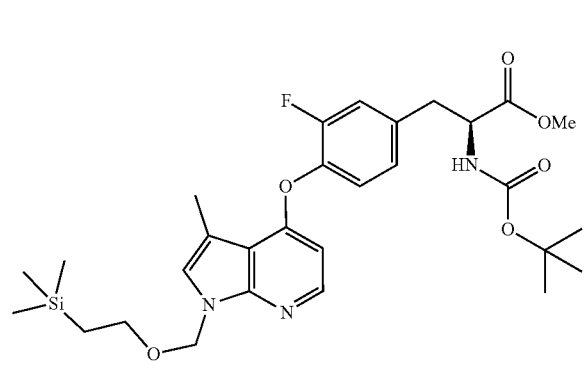 [SMILES: COC(=O)[C@H](Cc1ccc(Oc2ccnc3c2c(C)cn3COCC[Si](C)(C)C)c(F)c1)NC(=O)OC(C)(C)C]

Methyl (S)-2-((tert-butoxycarbonyl)amino)-3-(3-fluoro-4-((3-methyl-14(2-(tri-methylsilyl)ethoxy)methyl)-1H-pyrrolo [2,3-b]pyridin-4-yl)oxy)phenyl)-propanoate (Intermediate 1D-a)

A mixture of Intermediates 1B-a (5.96 g, 19.02 mmol) and 1C-a (6.09 g, 17.84 mmol), Pd2(dba)3 (0.82 g, 0.89 mmol), XPhos (0.85 g, 1.78 mmol), and potassium carbonate (5.42 g, 39.25 mmol) in toluene (224 mL) was sonicated for 5 min under a blanket of argon. The mixture was heated at 100° C. for 3 h, and then allowed to cool to RT before filtering through Celite®. The solvent was evaporated and the residue was taken up into water (40 mL) and extracted three times with ethyl acetate. The combined organic extracts were washed with brine, dried (Na2SO4) and evaporated. The crude product was chromatographed on a 300 g Si cartridge eluting with 0-50% ethyl acetate in cyclohexane. The product was obtained as a beige solid (4.85 g).

LCMS (Method 3): Rt=1.88 min, m/z 574.4 [M+H]+

Step E

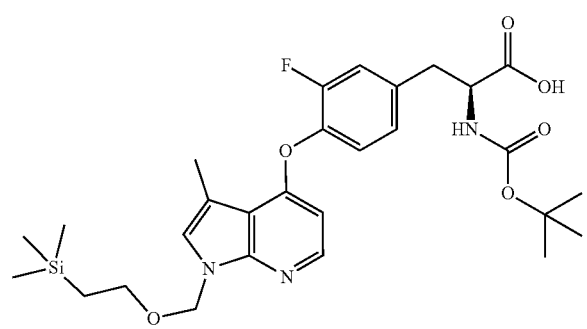 [SMILES: Cc1cn(COCC[Si](C)(C)C)c2nccc(Oc3ccc(C[C@H](NC(=O)OC(C)(C)C)C(=O)O)cc3F)c12]

(S)-2-((tert-Butoxycarbonyl)amino)-3-(3-fluoro-4-(3-methyl-14(2-(trimethylsilyl)ethoxy)methyl)-1H-pyrrolo [2,3-b]pyridin-4-yl)oxy)phenyl)propanoic acid (Intermediate 1E-a)

Intermediate 1D-a (4.85 g, 8.45 mmol) was dissolved in a mixture of methanol (42 mL), water (42 mL) and THF (21 mL). Lithium hydroxide hydrate (1.06 g, 25.35 mmol) was added and the reaction mixture was stirred at RT for 10 min. The solvent was reduced and the product was extracted three times with ethyl acetate. The combined organic extracts were washed with brine, dried (Na2SO4) and evaporated to give a beige solid (4.74 g).

LCMS (Method 4): Rt=1.79 min, m/z 560.4 [M+H]+

Step F

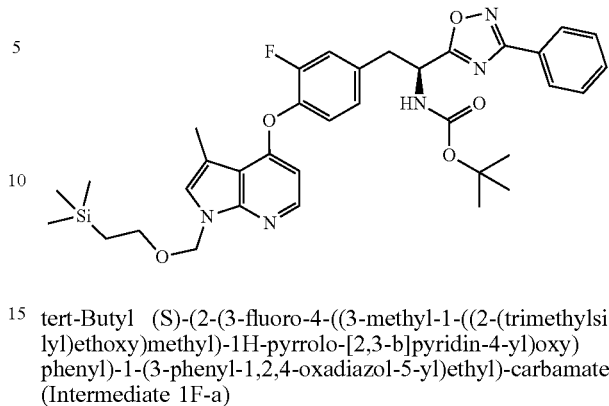

tert-Butyl (S)-(2-(3-fluoro-4-((3-methyl-1-((2-(trimethylsilyl)ethoxy)methyl)-1H-pyrrolo-[2,3-b]pyridin-4-yl)oxy) phenyl)-1-(3-phenyl-1,2,4-oxadiazol-5-yl)ethyl)-carbamate (Intermediate 1F-a)

Intermediate 1E-a (348 mg, 0.623 mmol), N-hydroxybenzimidamide (93 mg, 0.685 mmol), COMU (320 mg, 0.748 mmol) and DIPEA (388 μL, 2.24 mmol) in DCM (5 mL) were stirred under argon at RT overnight. The reaction mixture was diluted with toluene (20 mL) and heated at 120° C. for 100 min. The reaction mixture was cooled to RT, partitioned between DCM and brine, and separated on a hydrophobic frit before evaporation of the solvent. The crude material was purified by column chromatography on a 25 g Si cartridge eluting with 0-50% ethyl acetate in cyclohexane. Intermediate 1F-a was obtained as a light brown gum (190 mg).

LCMS (Method 3): Rt=1.97 min, m/z 660 [M+H]+

Step G

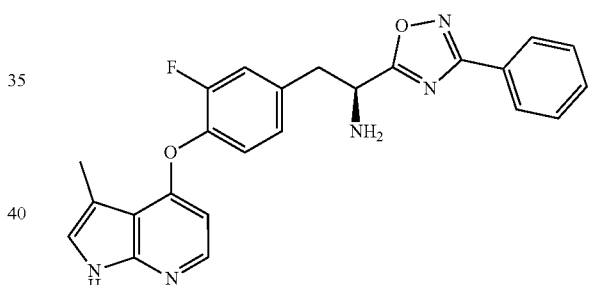

(S)-2-(3-fluoro-4((3-methyl-1H-pyrrolo[2,3-b]pyridin-4-yl) oxy)phenyl)-1-(3-phenyl-1,2,4-oxadiazol-5-yl)ethanamine (Example 1)

To a solution of Intermediate 1F-a (190 mg, 0.288 mmol) in DCM (6 mL) was added TFA (2 mL) and the reaction mixture was stirred at RT overnight. The crude material was evaporated then purified by MDAP and freeze-dried to give the title compound as a white solid (31 mg).

LCMS (Method 2): Rt=3.01 min, m/z 430.2 [M+H]+

$^1$H NMR (400 MHz, d6-DMSO) δ 11.38 (s, 1H), 8.03-7.99 (m, 2H), 7.93 (d, J=5.4 Hz, 1H), 7.61-7.56 (m, 3H), 7.38 (dd, J=1.9, 11.9 Hz, 1H), 7.22 (t, J=8.3 Hz, 1H), 7.16-7.10 (m, 2H), 6.11 (d, J=4.8 Hz, 1H), 4.54-4.43 (m, 1H), 3.25-3.10 (m, 2H), 2.36-2.34 (m, 5H).

ee >99% using chiral method 1.

Examples 2 to 8

The following Examples were prepared in a similar way to Example 1 by replacing at each step the appropriate starting materials.

Preparation of Intermediate 1B-b

The following intermediate was prepared in a similar manner to Intermediate 1B-a by replacing Intermediate 1A-a in Step B of Example 1 with the indicated starting material.

| Intermediate | Starting material | Starting material | LC-MS |
|---|---|---|---|
| 1B-b | (structure: Boc-protected methyl L-tyrosinate) | Methyl L-tyrosinate | Rt = 3.03 min, m/z 296.1 [M + H]+ (Method 5) |
| 1B-c | (structure: methyl 3-((Boc-amino)methyl)-2-(3-fluoro-4-hydroxybenzyl)propanoate) | Methyl 3-amino-2-(3-fluoro-4-hydroxybenzyl)-propanoate | Rt = 1.31 min, m/z 350.1 [M + Na]+ (Method 3) |

Preparation of Intermediate from 1C-b

Intermediate 1C-b was prepared in a similar manner to Intermediate 1C-a from the indicated starting material.

| Intermediate | Structure | Starting material | LC-MS |
|---|---|---|---|
| 1C-b | (structure: 4-bromo-1-((2-(trimethylsilyl)ethoxy)methyl)-7-azaindole) | 4-Bromo-7-azaindole | Rt = 1.80 min, m/z 326.9/328.9 [M + H]+ (Method 4) |

Preparation of Intermediates 1D-b and 1D-c

The following intermediates were prepared in a similar manner to Intermediate 1D-a from the starting materials indicated.

| Intermediate | Structure | Starting materials | LC-MS |
|---|---|---|---|
| 1D-b | (structure shown) | 1C-b and 1B-b | Rt = 4.67 min, m/z 542.3 [M + H]+ (Method 5) |

| Intermediate | Structure | Starting materials | LC-MS |
|---|---|---|---|
| 1D-c | [structure] | 1C-a and 1B-c | Rt = 1.89 min, m/z 588.5 [M + H]+ (Method 3) |

Preparation of Intermediates 1E-b and 1E-c

The following intermediates were prepared in a similar manner to Intermediate 1E-a from the indicated starting materials.

| Intermediate | Structure | Starting materials | LC-MS |
|---|---|---|---|
| 1E-b | [structure] | 1D-b | Rt = 4.24 min, m/z 528.4 [M + H]+ (Method 5) |
| 1E-c | [structure] | 1D-c | Rt = 1.80 min, m/z 574.4 [M + H]+ (Method 3) |

The following examples were prepared in a similar manner to Example 1 from the starting materials indicated.

| Ex | Structure | Starting materials | 1H NMR | LC-MS |
|---|---|---|---|---|
| 2 | 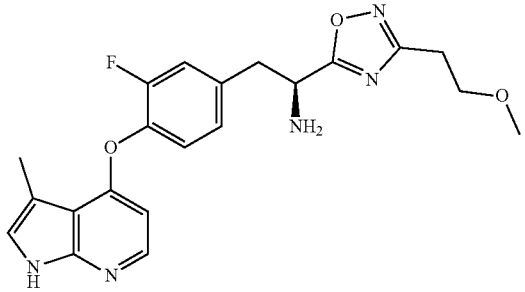<br>(S)-2-(3-fluoro-4-((3-methyl-1H-pyrrolo[2,3-b]pyridin-4-yl)oxy)phenyl)-1-(3-(2-methoxyethyl)-1,2,4-oxadiazol-5-yl)ethanamine | Intermediate 1E-a and N'-hydroxy-3-methoxypropan-imidamide hydrochloride | $^1$H NMR (400 MHz, d6-DMSO) δ 11.39 (s, 1H), 7.98 (d, J = 5.4 Hz, 1H), 7.30 (dd, J = 1.9, 11.9 Hz, 1H), 7.21 (t, J = 8.4 Hz, 1H), 7.16-7.11 (m, 1H), 7.09 (dd, J = 1.6, 8.2 Hz, 1H), 6.14 (dd, J = 0.8, 5.5 Hz, 1H), 4.36 (t, J = 6.6 Hz, 1H), 3.66 (t, J = 6.4 Hz, 2H), 3.22 (s, 3H), 3.15-3.02 (m, 2H), 2.91 (t, J = 6.3 Hz, 2H), 2.36 (d, J = 1.0 Hz, 3H), 2.24 (s, 2H). | Rt = 2.44 min, m/z 412.2 [M + H]+ (Method 2) ee >99% (chiral method 1) |
| 3 | 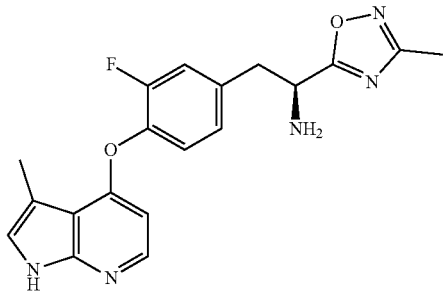<br>(S)-2-(3-fluoro-4-((3-methyl-1H-pyrrolo[2,3-b]pyridin-4-yl)oxy)phenyl)-1-(3-methyl-1,2,4-oxadiazol-5-yl)ethanamine | Intermediate 1E-a and N'-hydroxy-acetimidamide | $^1$H NMR (400 MHz, d6-DMSO) δ 11.39 (s, 1H), 7.99 (d, J = 5.4 Hz, 1H), 7.33 (dd, J = 1.9, 11.9 Hz, 1H), 7.25-7.19 (m, 1H), 7.16-7.12 (m, 1H), 7.10 (dd, J = 1.2, 8.4 Hz, 1H), 6.15 (dd, J = 0.8, 5.4 Hz, 1H), 4.35 (t, J = 7.2 Hz, 1H), 3.16-3.00 (m, 2H), 2.36 (d, J = 1.0 Hz, 3H), 2.32 (s, 3H), 2.24 (s, 2H). | Rt = 2.37 min, m/z 368.4 [M + H]+ (Method 2) ee 85% (chiral method 2) |
| 4 | 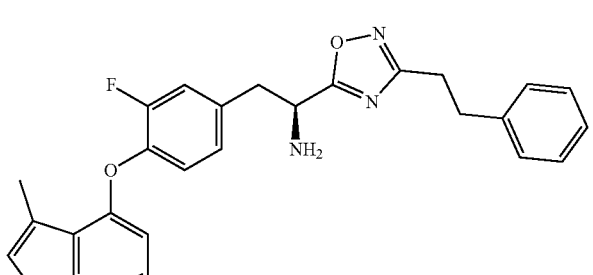<br>(S)-2-(3-fluoro-4-((3-methyl-1H-pyrrolo[2,3-b]pyridin-4-yl)oxy)phenyl)-1-(3-phenethyl-1,2,4-oxadiazol-5-yl)ethanamine | Intermediate 1E-a and N'-hydroxy-3-phenylpropan-imidamide | $^1$H NMR (400 MHz, d6-DMSO) δ 11.39 (s, 1H), 7.97 (d, J = 5.4 Hz, 1H), 7.32 (dd, J = 1.9, 11.8 Hz, 1H), 7.29-7.15 (m, 7H), 7.15-7.11 (m, 1H), 7.06 (dd, J = 1.3, 8.3 Hz, 1H), 6.14 (d, J = 5.0 Hz, 1H), 4.38 (t, J = 7.1 Hz, 1H), 3.12-3.06 (m, 2H), 2.97 (s, 3H), 2.36 (d, J = 1.0 Hz, 3H), 2.25 (s, 2H). | Rt = 3.11 min, m/z 458.3 [M + H]+ (Method 2) ee 93% (chiral method 3) |

| Ex | Structure | Starting materials | 1H NMR | LC-MS |
|---|---|---|---|---|
| 5 | 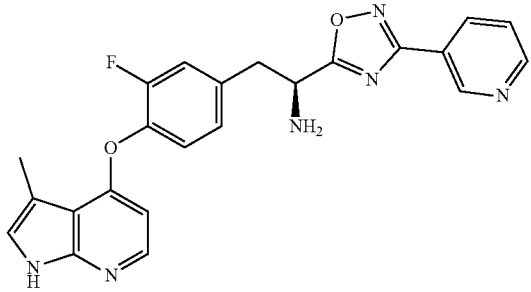<br>(S)-2-(3-fluoro-4-((3-methyl-1H-pyrrolo[2,3-b]pyridin-4-yl)oxy)phenyl)-1-(3-(pyridin-3-yl)-1,2,4-oxadiazol-5-yl)ethanamine | Intermediate 1E-a and N'-hydroxy-nicotin-imidamide | $^1$H NMR (400 MHz, d6-DMSO) δ 11.39 (s, 1H), 9.17 (d, J= 2.1 Hz, 1H), 8.79 (dd, J = 1.6, 4.8 Hz, 1H), 8.36 (td, J = 1.9, 8.0 Hz, 1H), 7.94 (d, J = 5.4 Hz, 1H), 7.62 (dd, J = 4.9, 7.9 Hz, 1H), 7.39 (dd, J = 1.9, 11.9 Hz, 1H), 7.25-7.12 (m, 3H), 6.12 (d, J = 5.4 Hz, 1H), 4.52 (t, J = 7.2 Hz, 1H), 3.25-3.11 (m, 2H), 2.36-2.35 (m, 5H). | Rt = 2.54 min, m/z 431.3 [M + H ]+ (Method 2) ee 48% (chiral method 3) |
| 6 | 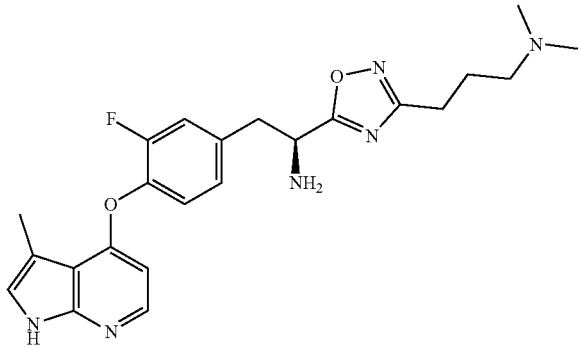<br>(S)-3-(5-(1-amino-2-(3-fluoro-4-((3-methyl-1H-pyrrolo[2,3-b]pyridin-4-yl)oxy)phenyl)ethyl)-1,2,4-oxadiazol-3-yl)-N,N-dimethylpropan-1-amine | Intermediate 1E-a and 4-(dimethylamino)-N'-hydroxy-butanimidamide | $^1$H NMR (400 MHz, d6-DMSO) δ 11.39 (s, 1H), 7.98 (d, J = 5.4 Hz, 1H), 7.29 (dd, J = 1.8, 11.8 Hz, 1H), 7.20 (t, J = 8.4 Hz, 1H), 7.15-7.12 (m, 1H), 7.09-7.05 (m, 1H), 6.13 (d, J = 5.4 Hz, 1H), 4.37 (t, J = 7.2 Hz, 1H), 3.13-3.03 (m, 2H), 2.67 (t, J = 7.4 Hz, 2H), 2.37-2.35 (m, 3H), 2.25 (s, 2H), 2.19 (t, J = 7.1 Hz, 2H), 2.09 (s, 6H), 1.78-1.70 (m, 2H). | Rt = 1.88 min, m/z 439.1 [M + H]+ (Method 1) ee 52% (chiral method 4) |
| 7 | 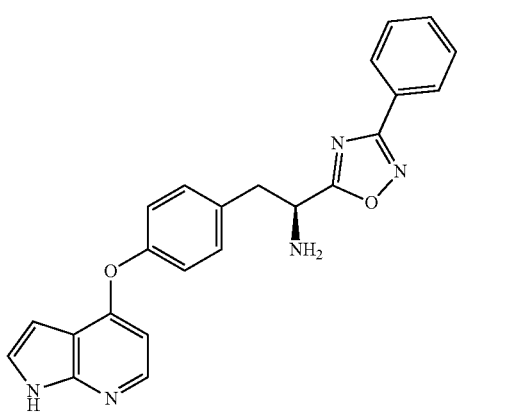<br>(S)-2-(4-((1H-pyrrolo[2,3-b]pyridin-4-yl)oxy)phenyl)-1-(3-phenyl-1,2,4-oxadiazol-5-yl)ethanamine | Intermediate 1E-b and N'-hydroxy-benzimidamide | $^1$H NMR (400 MHz, d6-DMSO) δ 11.69 (s, 1H), 8.02-7.98 (m, 3H), 7.60-7.56 (m, 3H), 7.30 (d, J = 8.6 Hz, 2H), 7.25 (dd, J = 2.5, 3.3 Hz, 1H), 7.07 (d, J = 8.8 Hz, 2H), 6.35 (d, J = 5.4 Hz, 1H), 6.08 (dd, J = 1.9, 3.5 Hz, 1H), 4.47 (s, 1H), 3.16 (d, J = 7.3 Hz, 2H), 2.33-2.32 (m, 2H). | Rt = 2.74 min, m/z 398.0 [M + H]+ (Method 1) ee 98% (chiral method 5) |

| Ex | Structure | Starting materials | 1H NMR | LC-MS |
|---|---|---|---|---|
| 8 | 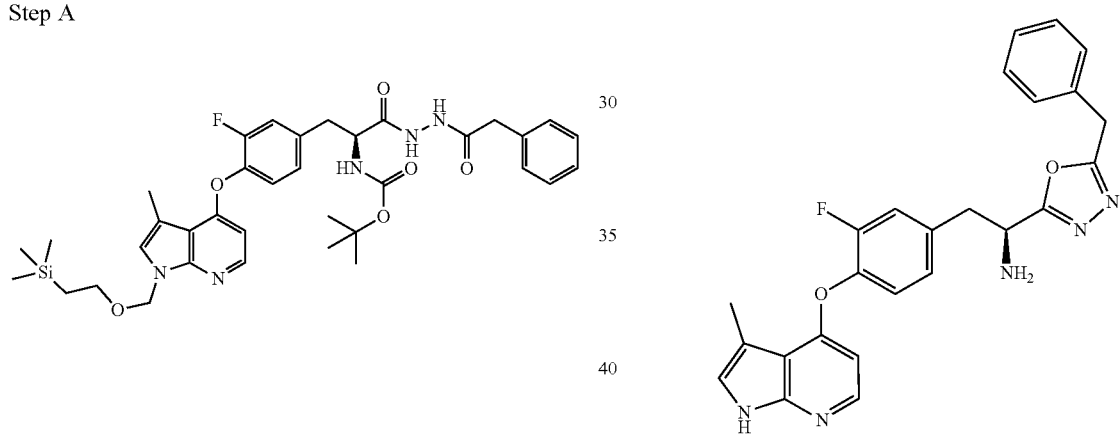<br>3-(3-fluoro-4-((3-methyl-1H-pyrrolo[2,3-b]pyridin-4-yl)oxy)phenyl)-2-(3-phenethyl-1,2,4-oxadiazol-5-yl)propan-1-amine | Intermediate 1E-c and N'-hydroxy-3-phenylpropan-imidamide | $^1$H NMR (400 MHz, d6-DMSO) δ 11.40 (s, 1H), 7.97 (d, J = 5.4 Hz, 1H), 7.30-7.13 (m, 8H), 7.02 (dd, J = 1.5, 8.2 Hz, 1H), 6.13 (d, J = 5.4 Hz, 1H), 3.48-3.40 (m, 1H), 3.16 (dd, J = 6.3, 13.7 Hz, 1H), 2.97-2.96 (m, 7H), 2.35 (d, J =0.9 Hz, 3H), 1.66 (s, 2H). | Rt = 3.03 min, m/z 472.4 [M + H]+ (Method 2) |

Example 9

Step A tert-Butyl (S)-(3-(3-fluoro-4-((3-methyl-14(2-(trimethylsilyl)ethoxy)methyl)-1H-pyrrolo [2,3-b]pyridin-4-yl)oxy)phenyl)-1-oxo-1-(2-(2-phenylacetyl)hydrazineyl)propan-2-yl)carbamate (Intermediate 9A)

Intermediate 1E-a (287 mg, 0.513 mmol), EDC.HCl (197 mg, 1.26 mmol) and HOBt (55 mg, 0.41 mmol) in DMF (3 mL) were stirred under argon at RT. 2-Phenylacetohydrazide (100 mg, 0.667 mmol) was added and the reaction mixture was stirred at RT overnight. The reaction mixture was diluted with water and stirred for 30 mins. The solid formed was collected by filtration and dried under vacuum at 50° C. overnight to afford Intermediate 9A as a white solid (189 mg).

LCMS (Method 3): Rt=1.94 min, m/z 692 [M+H]+

Step B (S)-1-(5-benzyl-1,3,4-oxadiazol-2-yl)-2-(3-fluoro-4-((3-methyl-1H-pyrrolo [2,3-b]pyridin-4-yl)oxy)phenyl) ethanamine (Example 9)

Intermediate 9A (185 mg, 0.276 mmol), p-toluenesulfonyl chloride (61 mg, 0.322 mmol) and PS-BEMP (2.2 mmol/g loading, 609 mg, 1.34 mmol) in THF (5 mL) were stirred under argon at reflux for 1 h 20 min. The reaction mixture was filtered and the filtrate was evaporated, dissolved in DMSO, and applied to a 2 g SCX-2 column. The column was washed with methanol then eluted with 2N ammonia in methanol. The methanol fraction was applied to a second 2 g SCX-2 column, washed with methanol then eluted with 2N ammonia in methanol. The ammonia fraction were combined and evaporated to a brown gum (113 mg). This material was dissolved in DCM (3 mL) and then treated with TFA (1.5 mL) and the reaction mixture was stirred under argon for 2 h. The mixture was diluted with methanol and applied to a 2 g methanol-wetted SCX-2 cartridge, washed with methanol then eluted with 2N ammonia in methanol. The ammonia fraction was left to stand overnight then evaporated. The crude material was purified by MDAP (basic) to give the title compound as a white solid (24 mg).

LCMS (Method 1): Rt=2.77 min, m/z 444.1 [M+H]+

$^1$H NMR (400 MHz, d6-DMSO) δ 11.42 (s, 1H), 7.99 (d, J=5.4 Hz, 1H), 7.35-7.25 (m, 6H), 7.18-7.13 (m, 2H), 6.99 (dd, J=1.4, 8.3 Hz, 1H), 6.14 (d, J=5.4 Hz, 1H), 4.63 (t, J=7.2 Hz, 1H), 4.27 (s, 2H), 3.14 (d, J=7.4 Hz, 2H), 2.36 (d, J=0.9 Hz, 3H).

ee >99% (chiral method 1)

Pharmacological Activity if the Compounds of the Invention.

In Vitro Inhibitory Activity Assay Description

The effectiveness of compounds of the invention to inhibit Rho kinase activity can be determined in a 10 μl assay containing 40 mM Tris pH7.5, 20 mM MgCl2 0.1 mg/ml BSA, 50 μM DTT and 2.5 μM peptide substrate (Myelin Basic Protein) using an ADP-Glo kit (Promega). Compounds were dissolved in DMSO such that the final concentration of DMSO was 1% in the assay. All reactions/incubations are performed at 25° C. Compound (2 ul) and either Rho kinase 1 or 2 (4 μl) were mixed and incubated for 30 mins. Reactions were initiated by addition of ATP (4 μl) such that the final concentration of ATP in the assay was 10 μM. After a 1 hour incubation 10 μl of ADP-Glo Reagent was added and after a further 45 minute incubation 20 ul of Kinase Detection Buffer was added and the mixture incubated for a further 30 minutes. The luminescent signal was measured on a luminometer. Controls consisted of assay wells that did not contain compound with background determined using assay wells with no enzyme added. Compounds were tested in dose-response format and the inhibition of kinase activity was calculated at each concentration of compound. To determine the IC50 (concentration of compound required to inhibit 50% of the enzyme activity) data were fit to a plot of % inhibition vs Log 10 compound concentration using a sigmoidal fit with a variable slope and fixing the maximum to 100% and the minimum to 0%. To determine the Ki values the Cheng-Prusoff equation was utilized (Ki=IC50/(1+[S]/Km)

Compounds according to the invention showed Ki values lower than 5 μM and for most of the compounds of the invention Ki is even lower that 500 nM.

The results for individual compounds are provided below in Table 2 and are expressed as range of activity.

TABLE 2

| Example | Activity ROCK1 | Activity ROCK2 |
|---|---|---|
| 1 | ++ | ++ |
| 2 | ++ | ++ |
| 3 | ++ | ++ |
| 4 | +++ | +++ |
| 5 | ++ | ++ |
| 6 | ++ | ++ |
| 7 | + | + |
| 8 | +++ | +++ |
| 9 | +++ | +++ | wherein the compounds are classified in term of potency with respect to their inhibitory activity on ROCK 1 ROCK 2 isoforms according to the following classification criterion:

+++:Ki<5 nM

++:Ki in the range 5-50 nM

+:Ki>50 nM.

The invention claimed is:

1. A compound of formula I

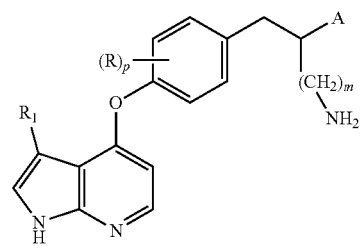

wherein p is zero or an integer from 1 to 3;

m is zero or an integer from 1 to 2;

A is an oxadiazole ring further substituted by R$_2$;

each R, when present, is an halogen;

R$_1$ is selected from the group consisting of:

—H, halogen,

—CN, and (C$_1$-C$_6$) alkyl,

R$_2$ is selected from the group consisting of:

—H, (C$_1$-C$_6$) alkyl, (C$_1$-C$_6$) haloalkyl, (C$_1$-C$_6$) hydroxyalkyl, (C$_1$-C$_6$) aminoalkyl, (C$_1$-C$_6$) alkoxy (C$_1$-C$_6$) alkyl, aryl, heteroaryl, and aryl(C$_1$-C$_6$)alkyl, each of said aryl and heteroaryl is further optionally substituted by one or more groups selected independently from halogen, —CN, —OH, (C$_1$-C$_8$)alkyl, (C$_1$-C$_6$) haloalkyl, (C$_1$-C$_{10}$)alkoxy, aryl, aryl(C$_1$-C$_6$)alkyl, carbamoyl, (C$_1$-C$_6$) aminoalkyl, (C$_1$-C$_6$) hydroxyalkyl, or pharmaceutically acceptable salts and solvates thereof.

2. The compound according to claim 1, wherein

A is an oxadiazole ring selected from the group consisting of

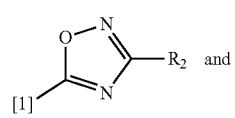

(Ia)

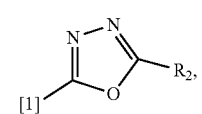

(Ib)

wherein [1] represents the point of attachment of the oxadiazole ring to the compound of formula I.

3. The compound of formula (I) according to claim 2, wherein
p is zero or 1;
m is zero or 1;
A is an oxadiazole ring selected from the group consisting of:

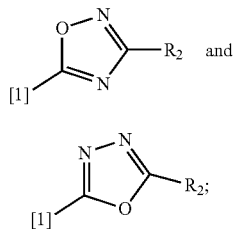

R, when present, is halogen;
R$_1$ is selected from the group consisting of:
—H, and
(C$_1$-C$_6$) alkyl;
R$_2$ is selected from the group consisting of:
(C$_1$-C$_6$) alkyl,
(C$_1$-C$_6$) aminoalkyl,
(C$_1$-C$_6$) alkoxy (C$_1$-C$_6$) alkyl,
aryl,
heteroaryl, and
aryl(C$_1$-C$_6$)alkyl.

4. The compound of formula (I) according to claim 3, wherein
p is zero or 1;
m is zero or 1;
A is an oxadiazole ring selected from the group consisting of:

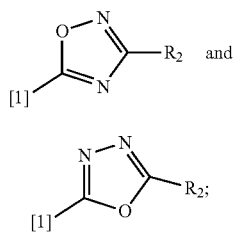

R, when present, is fluorine;
R$_1$ is —H or methyl,
R$_2$ is selected from the group consisting of:
methyl,
dimethylpropanamine,
methoxyethyl,
phenyl,
3-pyridinyl, and
phenylethyl and phenylmethyl.

5. The compound according to claim 1 selected from:
(S)-2-(3-fluoro-4-((3-methyl-1H-pyrrolo[2,3-b]pyridin-4-yl)oxy)phenyl)-1-(3-phenyl-1,2,4-oxadiazol-5-yl)ethanamine;
(S)-2-(3-fluoro-4-((3-methyl-1H-pyrrolo[2,3-b]pyridin-4-yl)oxy)phenyl)-1-(3-(2-methoxyethyl)-1,2,4-oxadiazol-5-yl)ethanamine;
(S)-2-(3-fluoro-4-((3-methyl-1H-pyrrolo[2,3-b]pyridin-4-yl)oxy)phenyl)-1-(3-methyl-1,2,4-oxadiazol-5-yl)ethanamine;
(S)-2-(3-fluoro-4-((3-methyl-1H-pyrrolo[2,3-b]pyridin-4-yl)oxy)phenyl)-1-(3-phenethyl-1,2,4-oxadiazol-5-yl)ethanamine;
(S)-2-(3-fluoro-4-((3-methyl-1H-pyrrolo[2,3-b]pyridin-4-yl)oxy)phenyl)-1-(3-(pyridin-3-yl)-1,2,4-oxadiazol-5-yl)ethanamine;
(S)-3-(5-(1-amino-2-(3-fluoro-4-(3-methyl-1H-pyrrolo[2,3-b]pyridin-4-yl)oxy)phenyl)ethyl)-1,2,4-oxadiazol-3-yl)-N,N-dimethylpropan-1-amine;
(S)-2-(4-((1H-pyrrolo[2,3-b]pyridin-4-yl)oxy)phenyl)-1-(3-phenyl-1,2,4-oxadiazol-5-yl)ethanamine;
3-(3-fluoro-4-((3-methyl-1H-pyrrolo[2,3-b]pyridin-4-yl)oxy)phenyl)-2-(3-phenethyl-1,2,4-oxadiazol-5-yl)propan-1-amine;
(S)-1-(5-benzyl-1,3,4-oxadiazol-2-yl)-2-(3-fluoro-4-(3-methyl-1H-pyrrolo[2,3-b]pyridin-4-yl)oxy)phenyl)ethanamine;
or pharmaceutically acceptable salts and solvates thereof.

6. A pharmaceutical composition comprising a compound according to claim 1, or a pharmaceutically acceptable salt thereof, either alone or in combination with another one or more active ingredients, in admixture with one or more pharmaceutically acceptable carriers or excipients.

7. The pharmaceutical composition according to claim 6 suitable to be administered by inhalation, wherein the pharmaceutical composition is selected from inhalable powders, propellant-containing metering aerosols or propellant-free inhalable formulations.

8. A method for treating a pulmonary disease in a subject in need thereof comprising administering the compound according to claim 1 to the subject.

9. A method for treating a pulmonary disease in a subject comprising administering to the subject the compound according to claim 1, wherein the pulmonary disease is selected from the group consisting of asthma, chronic obstructive pulmonary disease (COPD), idiopathic pulmonary fibrosis (IPF), and pulmonary hypertension (PH).

10. A combination of a compound according to claim 1 with one or more active ingredients selected from the classes consisting of organic nitrates; NO donors; inhaled NO; stimulator of soluble guanylate cyclase (sGC); prostacyclin analogue PGI2; agonist of prostacyclin receptors; compounds that inhibit the degradation of cyclic guanosine monophosphate (cGMP) and/or cyclic adenosine monophosphate (cAMP); human neutrophilic elastase inhibitors; compounds inhibiting the signal transduction cascade; active substances for lowering blood pressure; neutral endopeptidase inhibitors; osmotic agents; ENaC blockers; anti-inflammatories; corticosteroids; antagonists of chemokine receptors; bronchodilators; antihistamine drugs; anti-tussive drugs; antibiotics; DNase drug substances; selective cleavage agents; agents that inhibit ALK5 and/or ALK4 phosphorylation of Smad2 and Smad3; tryptophan hydroxylase 1 (TPH1) inhibitors; and multi-kinase inhibitors.

11. A device comprising the pharmaceutical composition according to claim 6, which is a single- or multi-dose dry powder inhaler, a metered dose inhaler, or a soft mist nebulizer.

12. A pharmaceutical composition comprising a compound according to claim 5, or a pharmaceutically acceptable salt thereof, either alone or in combination with another one or more active ingredients, in admixture with one or more pharmaceutically acceptable carriers or excipients.

13. The pharmaceutical composition according to claim 12 suitable to be administered by inhalation, wherein the pharmaceutical composition is selected from inhalable powders, propellant-containing metering aerosols or propellant-free inhalable formulations.

14. A method for treating a pulmonary disease in a subject in need thereof comprising administering the compound according to claim 5 to the subject.

15. A method for treating a pulmonary disease in a subject comprising administering to the subject the compound according to claim 5, wherein the pulmonary disease is selected from the group consisting of asthma, chronic obstructive pulmonary disease (COPD), idiopathic pulmonary fibrosis (IPF), pulmonary hypertension (PH).

16. A combination of a compound according to claim 5 with one or more active ingredients selected from the classes consisting of organic nitrates; NO donors; inhaled NO; stimulator of soluble guanylate cyclase (sGC); prostacyclin analogue PGI2; agonist of prostacyclin receptors; compounds that inhibit the degradation of cyclic guanosine monophosphate (cGMP) and/or cyclic adenosine monophosphate (cAMP); human neutrophilic elastase inhibitors; compounds inhibiting the signal transduction cascade; active substances for lowering blood pressure; neutral endopeptidase inhibitors; osmotic agents; ENaC blockers; anti-inflammatories; corticosteroids; antagonists of chemokine receptors; bronchodilators; antihistamine drugs; anti-tussive drugs; antibiotics; DNase drug substances; selective cleavage agents; agents that inhibit ALK5 and/or ALK4 phosphorylation of Smad2 and Smad3; tryptophan hydroxylase 1 (TPH1) inhibitors; and multi-kinase inhibitors.

17. A device comprising the pharmaceutical composition according to claim 12, which is a single- or multi-dose dry powder inhaler, a metered dose inhaler, or a soft mist nebulizer.

18. A method for treating a pulmonary disease in a subject in need thereof comprising administering the pharmaceutical composition according to claim 6 to the subject.

19. A method for treating a pulmonary disease in a subject comprising administering to the subject the pharmaceutical composition according to claim 6, wherein the pulmonary disease is selected from the group consisting of asthma, chronic obstructive pulmonary disease (COPD), idiopathic pulmonary fibrosis (IPF), and pulmonary hypertension (PH).

20. A method for treating a pulmonary disease in a subject in need thereof comprising administering the pharmaceutical composition according to claim 12 to the subject.

21. The method of claim 9, wherein the pulmonary disease is Pulmonary Arterial Hypertension (PAH).

22. The method of claim 15, wherein the pulmonary disease is Pulmonary Arterial Hypertension (PAH).

23. The method of claim 19, wherein the pulmonary disease is Pulmonary Arterial Hypertension (PAH).

* * * * *